(12) United States Patent
Gillet et al.

(10) Patent No.: US 9,598,406 B2
(45) Date of Patent: Mar. 21, 2017

(54) QUINAZOLINONE DERIVATIVES FOR USE IN THE TREATMENT OF CHLAMYDIALES INFECTIONS

(71) Applicant: Commissariat a l'Energie Atomique et aux Energies Alternatives, Paris (FR)

(72) Inventors: Daniel Gillet, Antony (FR); Julien Barbier, Gif-sur-Yvette (FR); Jean-Christophe Cintrat, Igny (FR); Karen Hinsinger, Massy (FR); Thomas Rudel, Würzburg (DE); Jo-Ana Herweg, Würzburg (DE); Annette Fischer, Würzburg (DE)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 15/134,371

(22) Filed: Apr. 20, 2016

(65) Prior Publication Data

US 2016/0311815 A1    Oct. 27, 2016

(30) Foreign Application Priority Data

Apr. 21, 2015   (EP) ..................... 15305601

(51) Int. Cl.
   *C07D 417/14*    (2006.01)
   *C07D 409/04*    (2006.01)
   *A61K 31/517*    (2006.01)

(52) U.S. Cl.
   CPC .......... *C07D 417/14* (2013.01); *A61K 31/517* (2013.01); *C07D 409/04* (2013.01)

(58) Field of Classification Search
   CPC ........................... C07D 417/14; A61K 31/517

USPC .................................................. 514/266.24
See application file for complete search history.

(56) References Cited

FOREIGN PATENT DOCUMENTS

WO    2014/014814 A1    1/2014
WO    2014/060586 A1    4/2014

OTHER PUBLICATIONS

European Search Report issued in corresponding European Patent Application No. 15305601 dated Jun. 26, 2015.
Aeberhard, "Isolation and proteomic characterization of the mid-infection inclusion of Chlamydia trachomatis," 1-175 (2014).
Park et al., "Chemical Structure of Retro-2, a Compound that Protects Cells against Ribosome-Inactivating Proteins," Scientific Reports, 2: 631 (2012).

*Primary Examiner* — Yevegeny Valenrod
(74) *Attorney, Agent, or Firm* — Morgan, Lewis & Bockius LLP

(57) ABSTRACT

The present invention relates to a method for treating a Chlamydiae infection comprising the administration of a therapeutically effective amount of a compound of formula (I) to a subject in need thereof:

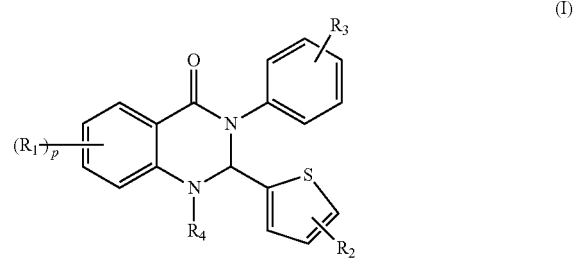

Wherein, R1, R2, R3, R4 and p are as defined in claim 1.

13 Claims, 5 Drawing Sheets

QUINAZOLINONE DERIVATIVES FOR USE IN THE TREATMENT OF CHLAMYDIALES INFECTIONS

The present invention is in the field of therapeutic drugs to treat intracellular bacterial infection and disease. In particular, the invention provides quinazolinone compounds for use in the treatment of infections by pathogenic intracellular bacteria in the order Chlamydiales.

The bacterial order Chlamydiales includes only obligately intracellular bacteria that have a *chlamydia*-like developmental cycle of replication. Chlamydiales live in animals, insects, and protozoa. The order Chlamydiales belongs to the class Chlamydiae, phylum Chlamydiae, domain Bacteria.

Chlamydiales order display a stereotypical developmental cycle that alternates between two forms. The elementary body (EB) is the infectious form that attaches to and invades target epithelial cells. After entry, the EB form transitions to a reticulate body (RB), which proliferates within the expanding parasitophorous vacuole, termed the inclusion (Field & Hackstadt 2002). Upon triggering by an undefined signal, RBs transition to infectious progeny, which are later released to the surrounding milieu either by lysis or an extrusion mechanism, to infect new host cells (Hybiske & Stephens 2007).

Currently, the order Chlamydiales includes the families Chlamydiaceae, Simkaniaceae and Waddliaceae, which have Gram-negative extracellular infectious bodies (EBs), and Parachlamydiaceae, which has variable Gram staining of EBs.

Mammalian pathogenic bacteria from Chlamydiales order include *Chlamydia trachomatis* responsible for genital, ocular and lung infections; *Chlamydophila pneumoniae* responsible for a pneumonia and associated with asthma; *Chlamydophila psittaci* responsible for a pneumonia transmitted to humans by birds; *Simkania negevensis* is associated with infections of the upper respiratory tract in infants and adults.

*Chlamydia trachomatis* (Ctr) is an obligate intracellular human pathogen and one of the main causative agents of sexually transmitted diseases (STD). Infections of the eye with Ctr can lead to chronic conjunctivitis (trachoma) resulting in preventable blindness if untreated. The WHO estimates around 540 million people suffering from Ctr ocular infection whereby 1.2 million people developed blindness (Resnikoff, S., et al., Global data on visual impairment in the year 2002. Bull World Health Organ, 2004. 82(11): p. 844-51).

Alternatively, infections of the urogenital tract cause prostatitis, pelvic inflammatory disease and in women increased risk of ectopic pregnancy or infertility. The number of urogenital tract infections with Ctr worldwide in 2008 was estimated by the WHO to about 106 million cases.

As many as half of all infants born to mothers with *chlamydia* will be born with the disease. *Chlamydia* can affect infants by causing spontaneous abortion; premature birth; conjunctivitis, which may lead to blindness; and pneumonia. *Chlamydia* may also cause reactive arthritis (Reiters' syndrome)—the triad of arthritis, conjunctivitis and urethritis (inflammation of the urethra)—especially in young men. About 15,000 men develop reactive arthritis due to *chlamydia* infection each year in the U.S., and about 5,000 are permanently affected by it. It can occur in both sexes, though is more common in men.

Although antibiotics resistance is considered rare for *Chlamydia trachomatis*, it is widespread in several sexually transmitted bacteria, e.g. *Neisseria gonorrhoeae* or *Mycoplasma genitalium* (Unemo, M. and W. M. Shafer, Antibiotic resistance in *Neisseria gonorrhoeae*: origin, evolution, and lessons learned for the future. Ann NY Acad Sci, 2011. 1230: p. E19-28). The rapid spread of Azithromycin resistances among these bacteria has been attributed to the frequent treatment of patients with chlamydial infection with this antibiotic (Unemo, M. and W. M. Shafer, Antibiotic resistance in *Neisseria gonorrhoeae*: origin, evolution, and lessons learned for the future. Ann NY Acad Sci, 2011. 1230: p. E19-28; Ison, C., Antimicrobial resistance in sexually transmitted infections in the developed world: implications for rational treatment. Curr Opin Infect Dis., 2012). Development of treatment regimens more specific for particular pathogens without affecting others has been suggested as one strategy to avoid the continuous spread of antibiotic resistances.

Species in the family Simkaniaceae Parachlamydiaceae and Waddliaceae have a *chlamydia*-like cycle of replication. They may infect humans and give respiratory diseases; they currently include two genera: *Simkania* and *Fritschea*.

Parachlamydiaceae such as *Parachlamydia acanthamoebae* have been found in the respiratory tract of humans and could be important respiratory pathogens. Waddliaceae can provoke abortion in ruminants. Two *Fritschea* species have been identified in insects. *Piscichlamydia salmonis* has recently been identified as an agent of the gill epitheliocystis in the Atlantic salmon.

The genome of *Simkania negevensis* (Sn) is approximately 2.5 Mbp in size and thus 2-3 times larger than the genome of *Chlamydia* (Collingro A, Tischler P, Weinmaier T, Penz T, Heinz E, Brunham R C, Read T D, Bavoil P M, Sachse K, Kahane S, Friedman M G, Rattei T, Myers G S, Horn M. Unity in variety—the pan-genome of the Chlamydiae. Mol Biol Evol 2011; 28(12):3253-3270). Sn is able to replicate in several amoebae, human and simian epithelial cells and macrophages (Kahane S, Fruchter D, Dvoskin B, Friedman M G. Versatility of *Simkania negevensis* infection in vitro and induction of host cell inflammatory cytokine response. J Infect 2007; 55(2):e13-21; Kahane S, Gonen R, Sayada C, Elion J, Friedman M G. Description and partial characterization of a new *Chlamydia*-like microorganism. FEMS Microbiol Lett 1993; 109(2-3):329-333) and has been associated with infections of the upper respiratory tract in infants and adults (Horn M. Chlamydiae as Symbionts in Eukaryotes. Annu Rev Microbiol 2008; 62:113-131; Kahane S, Greenberg D, Friedman M G, Haikin H, Dagan R. High prevalence of "*Simkania Z*" a novel *Chlamydia*-like bacterium in infants with acute bronchiolitis. (vol 177, pg 1425, 1998). J Infect Dis 1998; 178(5):1553-1553; Lieberman D, Kahane S, Lieberman D, Friedman M G. Pneumonia with serological evidence of acute infection with the *Chlamydia*-like microorganism "Z". Am J Respir Crit Care Med 1997; 156(2 Pt 1):578-582; Lamoth F, Greub G. Amoebal pathogens as emerging causal agents of pneumonia. Fems Microbiol Rev 2010; 34(3):260-280).

Infections with the two closely related human pathogenic bacteria *Chlamydophila pneumoniae* and *Chlamydophila psittaci* can cause community acquired or animal transmitted pneumonia, chronic bronchitis and chronic asthma (Harkinezhad T, Geens T, Vanrompay D. *Chlamydophila psittaci* infections in birds: A review with emphasis on zoonotic consequences. Vet Microbiol 2009; 135(1-2):68-77; Hughes C, Maharg P, Rosario P, Herrell M, Bratt D, Salgado J, Howard D. Possible nosocomial transmission of psittacosis. Infect Control Hosp Epidemiol 1997; 18(3):165-168; Hahn D L, McDonald R. Can acute *Chlamydophila pneumoniae* respiratory tract infection initiate chronic asthma, Ann Allergy Asthma Immunol 1998; 81(4):339-344).

Accordingly, it is an object of the present invention to provide compounds alternative to conventional antibiotics useful for preventing and/or treating infections by bird, fish and mammalian, preferably human and zoonotic, pathogenic Chlamydiales.

Inventors have for the first time demonstrated that a selection of cycloamine derivatives shows a strong inhibition of infections with pathogenic bacteria in the order of Chlamydiales.

In particular, Inventors have found that compounds of formula (I') are surprisingly highly potent at low concentration and affect cellular mechanisms that are important at defined stages of the chlamydial developmental cycle.

Compounds of Formula (I) for Use in the Treatment of Chlamidyales Infection

Thus, in one aspect, the present invention relates to a compound of formula (I)

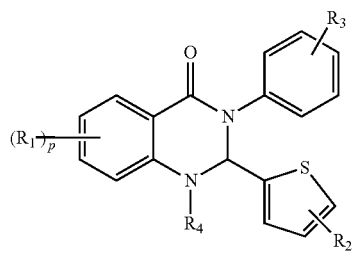

Wherein:
$R_1$ is at each occurrence, independently selected from H, Cl, Br, I, F;
$R_2$ is independently selected from H, Cl, Br, F, I, $C_1$-$C_6$ alkyl, $C_6$-$C_{10}$ aryl, 5 to 10 membered heteroaryl, said aryl or heteroaryl groups being optionally substituted by one to three $R_5$;
$R_3$ is independently selected from H, F, Cl, Br, I, $C_1$-$C_6$ alkyl;
$R_4$ is, at each occurrence, independently selected from H, $C_1$-$C_6$ alkyl;
$R_5$ is independently selected from F, Cl, Br, I, $C_1$-$C_6$ alkyl, $C_6$-$C_{10}$ aryl, said aryl group being optionally substituted by one to three $R_6$;
$R_6$ is F, Cl, Br, I;
p is 1, 2 or 3,
and the stereoisomeric forms, mixtures of stereoisomeric forms or pharmaceutically acceptable salts forms thereof,
for use in the treatment of a Chlamydiae infection.

In another aspect, the present invention relates to a compound of formula (I)

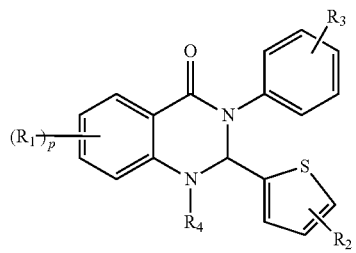

Wherein:
$R_1$ is at each occurrence, independently selected from H, Cl, Br, I, F;
$R_2$ is independently selected from H, Cl, Br, F, I, $C_1$-$C_6$ alkyl, $C_6$-$C_{10}$ aryl, 5 to 10 membered heteroaryl, said aryl or heteroaryl groups being optionally substituted by one to three $R_5$;
$R_3$ is independently selected from H, F, Cl, Br, I, $C_1$-$C_6$ alkyl;
$R_4$ is, at each occurrence, independently selected from H, $C_1$-$C_6$ alkyl;
$R_5$ is independently selected from F, Cl, Br, I, $C_1$-$C_6$ alkyl, $C_6$-$C_{10}$ aryl, said aryl group being optionally substituted by one to three $R_6$;
$R_6$ is F, Cl, Br, I;
p is 1, 2 or 3,
and the stereoisomeric forms, mixtures of stereoisomeric forms or pharmaceutically acceptable salts forms thereof,
providing said compound is not of the following formula:

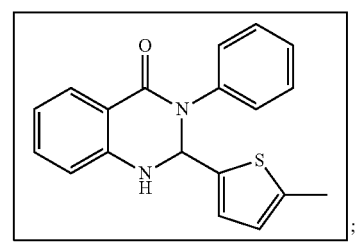

for use in the treatment of a Chlamydiae infection.

In a preferred embodiment, the Chlamydiae infection is a *Chlamydia* or *Simkania* infection.

In another embodiment, there are included compounds of formula (I) for use as defined above, wherein at least one of $R_1$ is H or F.

In still another embodiment, there are included compounds of formula (I') for use as defined above, which are compounds of formula (I) wherein $R_2$ is independently selected from H, Cl, Br, F, I, $C_6$-$C_{10}$ aryl, 5 to 10 membered heteroaryl, said aryl or heteroaryl groups being optionally substituted by one to three $R_5$, $R_5$ being as defined above.

In still another embodiment, there are included compounds of formula (I) for use as defined above, wherein $R_2$ is a 5 to 10 membered heteroaryl.

In yet another embodiment, there are included compounds of formula (I) for use as defined above, wherein $R_2$ is 1,3-thiazolyl, preferably 4-(1,3-thiazolyl).

In an additional embodiment, there are included compounds of formula (I) for use as defined above, wherein $R_3$ is H.

In an additional embodiment, there are included compounds of formula (I) for use as defined above, wherein $R_4$ is H.

In another additional embodiment, there are included compounds of formula (I) for use as defined above, wherein $R_4$ is $C_1$-$C_6$ alkyl, notably methyl.

In a particular embodiment, there are included compounds of formula (I) for use as defined above, which are selected from:

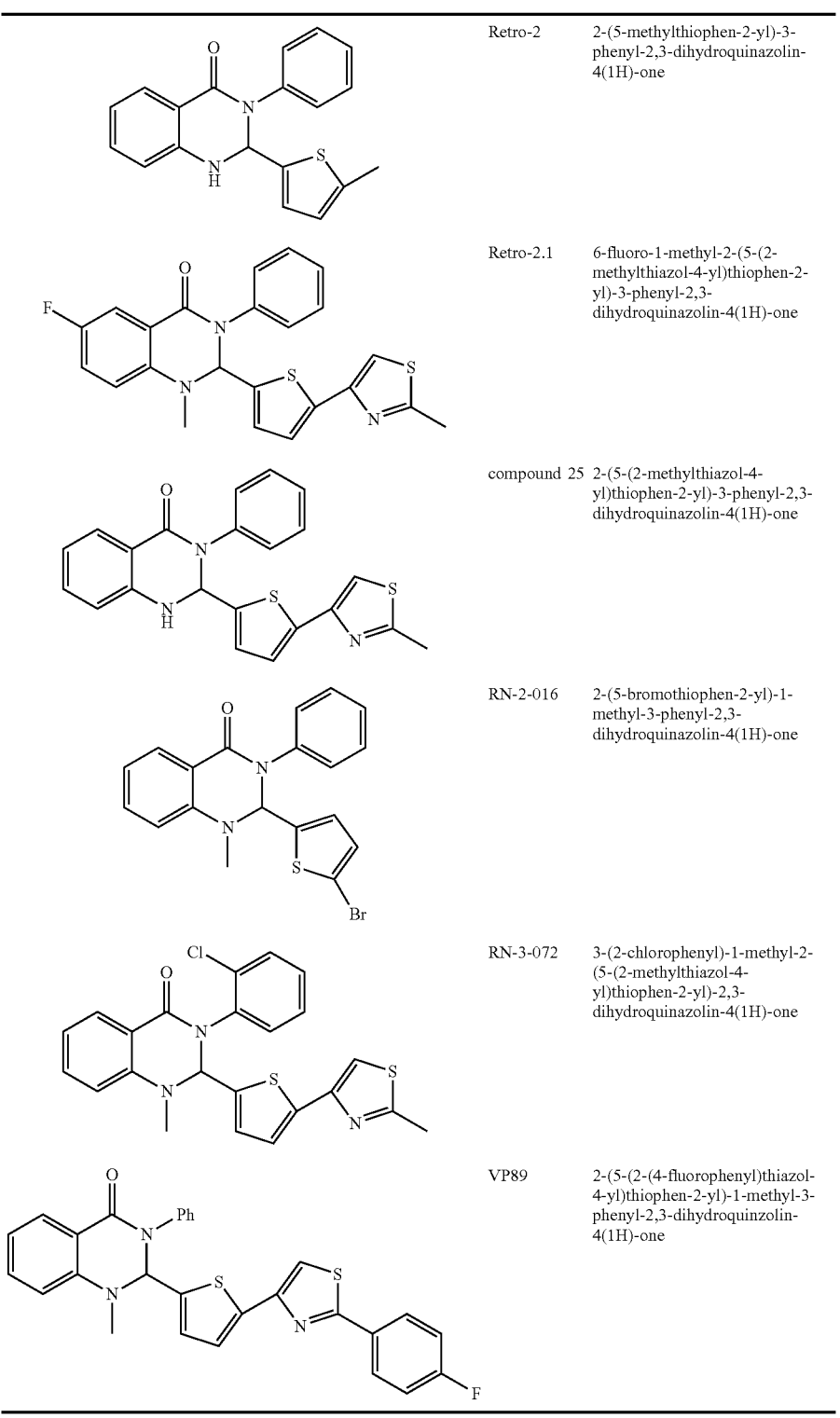

| | | |
|---|---|---|
| | Retro-2 | 2-(5-methylthiophen-2-yl)-3-phenyl-2,3-dihydroquinazolin-4(1H)-one |
| | Retro-2.1 | 6-fluoro-1-methyl-2-(5-(2-methylthiazol-4-yl)thiophen-2-yl)-3-phenyl-2,3-dihydroquinazolin-4(1H)-one |
| | compound 25 | 2-(5-(2-methylthiazol-4-yl)thiophen-2-yl)-3-phenyl-2,3-dihydroquinazolin-4(1H)-one |
| | RN-2-016 | 2-(5-bromothiophen-2-yl)-1-methyl-3-phenyl-2,3-dihydroquinazolin-4(1H)-one |
| | RN-3-072 | 3-(2-chlorophenyl)-1-methyl-2-(5-(2-methylthiazol-4-yl)thiophen-2-yl)-2,3-dihydroquinazolin-4(1H)-one |
| | VP89 | 2-(5-(2-(4-fluorophenyl)thiazol-4-yl)thiophen-2-yl)-1-methyl-3-phenyl-2,3-dihydroquinzolin-4(1H)-one |

In a particular embodiment, there are included compounds of formula (I) for use as defined above, which are selected from:

6-fluoro-1-methyl-2-(5-(2-methylthiazol-4-yl)thiophen-2-yl)-3-phenyl-2,3-dihydroquinazolin-4(1H)-one (Retro 2.1)

2-(5-(2-methylthiazol-4-yl)thiophen-2-yl)-3-phenyl-2,3-dihydroquinazolin-4(1H)-one (Compound 25)

2-(5-bromothiophen-2-yl)-1-methyl-3-phenyl-2,3-dihydroquinazolin-4(1H)-one (RN 2-016)

3-(2-chlorophenyl)-1-methyl-2-(5-(2-methylthiazol-4-yl)thiophen-2-yl)-2,3-dihydroquinazolin-4(1H)-one (RN 3-072)

2-(5-(2-(4-fluorophenyl)thiazol-4-yl)thiophen-2-yl)-1-methyl-3-phenyl-2,3-dihydroquinazolin-4(1H)-one (VP 89).

The present invention also relates to a method of treatment comprising the administration of a therapeutically effective amount of a compound of formula (I) to a subject in need thereof.

The compounds of formula (I) are useful for the treatment of infection with pathogenic bacteria, preferably mammalian pathogenic bacteria, more preferably human pathogenic bacteria, in the order of Chlamydiales; in particular, for the treatment of infection with bacteria in the genus of *Chlamydia*, such as *Chlamydia trachomatis, Chlamydophila pneumoniae, Chlamydophila psyttaci* . . . , or *Symkania*, such as *Symkania negevensis* . . . .

According to one embodiment, the present invention relates to compounds of formula (I) for their use for the treatment of:
- respiratory tract infection, such as bronchiolitis, pneumonia, bronchitis, asthma, with *Chlamydophila pneumoniae, Chlamydophila psyttaci* (responsible for a pneumonia transmitted to humans by birds) and/or *Symkania negevensis* (infections of the upper respiratory tract in infants and adults); lung infection with *Chlamydia* trachomatis;
- ocular infection, such as conjunctivitis, with *Chlamydia trachomatis;*
- urogenital tract infection, such as prostatitis, pelvic inflammation, urethritis, sexually transmitted disease (STD) with *Chlamydia trachomatis;*
- arthritis;

and for the prevention of:
- blindness induced by ocular infection with *Chlamydia trachomatis;*
- ectopic pregnancy, infertility, spontaneous abortion, premature birth induced by urogenital tract infection with *Chlamydia trachomatis.*

According to another embodiment, the present invention relates to compounds of formula (I) for their use to inhibit primary and progeny infection of *Symkania*.

A primary infection is the initial infection of a host by a pathogen, here infectious bacteria in the order of Chlamydiales.

A progeny infection is the infection of new host cells by the infectious bacteria released after a previous primary infection of a host cell.

According to a further embodiment, the present invention relates to compounds of formula (I) for their use to inhibit primary and progeny infection of *Chlamydia*.

Pharmaceutical Compositions

In a second aspect, the present invention relates to a pharmaceutical composition comprising a compound of formula (Ia):

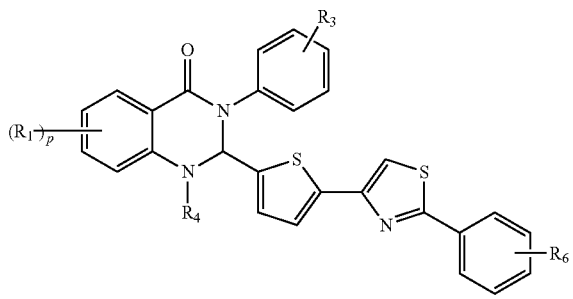

(Ia)

Wherein:
$R_1$, $R_3$, $R_4$, $R_6$, and p are as defined in formula (I) above,
$R_4$ is independently selected from H or $C_1$-$C_6$ alkyl, and the stereoisomeric forms, mixtures of stereoisomeric forms or pharmaceutically acceptable salts forms thereof,
in admixture with one or more pharmaceutically acceptable excipients.

In one embodiment, there are included pharmaceutical compositions wherein, in formula (Ia), $R_4$ is $C_1$-$C_6$ alkyl, notably methyl.

In another embodiment, there are included pharmaceutical compositions wherein, in formula (Ia), $R_4$ is H.

In another embodiment, there are included pharmaceutical compositions wherein, in formula (Ia), wherein $R_3$ is H.

In still another embodiment, there are included pharmaceutical compositions wherein, in formula (Ia), $R_1$ is H. In yet another embodiment, there are included pharmaceutical compositions wherein the compound of formula (Ia) is: 2-(5-(2-(4-fluorophenyl)thiazol-4-yl)thiophen-2-yl)-1-methyl-3-phenyl-2,3-dihydroquinazolin-4(1H)-one (VP89).

The compounds of formula (I) and/or (Ia) of the present invention may be administered in the form of a conventional pharmaceutical composition by any route including orally, intramuscularly, subcutaneously, topically, intranasally, intraperitoneally, intrathoracially, intravenously, epidurally, intrathecally, intracerebroventricularly and by injection into the joints.

The dosage will depend on the route of administration, the severity of the disease, age and weight of the patient and other factors normally considered by the attending physician, when determining the individual regimen and dosage level at the most appropriate for a particular patient.

For preparing pharmaceutical compositions from the compounds of the present invention, inert, pharmaceutically acceptable carriers can be either solid or liquid. Solid form preparations include powders, tablets, dispersible granules, capsules, cachets, and suppositories.

A solid carrier can be one or more substances, which may also act as diluents, flavouring agents, solubilizers, lubricants, suspending agents, binders, or tablet disintegrating agents; it can also be an encapsulating material.

Tablets, powders, cachets, and capsules can be used as solid dosage forms suitable for oral administration.

Liquid form compositions include solutions, suspensions, and emulsions. For example, sterile water or propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavouring agents, stabilizers, and thickening agents as desired. Aqueous solutions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Depending on the mode of administration, the pharmaceutical composition will according to one embodiment of the present invention include 0.05% to 99% weight (percent by weight), according to an alternative embodiment from 0.10 to 50% weight, of the compound of the present invention, all percentages by weight being based on total composition. A therapeutically effective amount for the practice of the present invention may be determined, by the use of known criteria including the age, weight and response of the individual patient, and interpreted within the context of the disease which is being treated or which is being prevented, by one of ordinary skills in the art.

Compounds of Formula (Ia)

In a third aspect, the present invention relates to a compound of formula (Ia) as defined above, and the stereoisomeric forms, mixtures of stereoisomeric forms or pharmaceutically acceptable salts forms thereof.

It is to be noted that the present invention includes the combination of all the embodiments listed hereabove for formulae (I) or (Ia), respectively.

Definitions

The following terms and expressions contained herein are defined as follows:

As used herein, a range of values in the form "x-y" or "x to y", or "x through y", include integers x, y, and the integers therebetween. For example, the phrases "1-6", or "1 to 6" or "1 through 6" are intended to include the integers 1, 2, 3, 4, 5, and 6. Preferred embodiments include each individual integer in the range, as well as any subcombination of integers. For example, preferred integers for "1-6" can include 1, 2, 3, 4, 5, 6, 1-2, 1-3, 1-4, 1-5, 2-3, 2-4, 2-5, 2-6, etc.

As used herein, the term "alkyl" refers to a straight-chain, or branched alkyl group having 1 to 8 carbon atoms, such as methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, octyl, etc. The alkyl moiety of alkyl-containing groups, such as alkoxy, alkoxycarbonyl, and alkylaminocarbonyl groups, has the same meaning as alkyl defined above. Lower alkyl groups, which are preferred, are alkyl groups as defined above which contain 1 to 4 carbons. A designation such as "$C_1$-$C_4$ alkyl" refers to an alkyl radical containing from 1 to 4 carbon atoms.

As used herein, the term "aryl" refers to a substituted or unsubstituted, mono- or bicyclic hydrocarbon aromatic ring system having 6 to 10 ring carbon atoms. Examples include phenyl and naphthyl. Preferred aryl groups include unsubstituted or substituted phenyl and naphthyl groups. Included within the definition of "aryl" are fused ring systems, including, for example, ring systems in which an aromatic ring is fused to a cycloalkyl ring. Examples of such fused ring systems include, for example, indane, indene, and tetrahydronaphthalene.

As used herein, the term "heteroaryl" refers to an aromatic group containing 5 to 10 ring carbon atoms in which one or more ring carbon atoms are replaced by at least one hetero atom such as —O—, —N—, or —S—. Examples of heteroaryl groups include pyrrolyl, furanyl, thienyl, pirazolyl, imidazolyl, thiazolyl, isothiazolyl, isoxazolyl, oxazolyl, oxathiolyl, oxadiazolyl, triazolyl, oxatriazolyl, furazanyl, tetrazolyl, pyridyl, pyrazinyl, pyrimidinyl, pyridazinyl, triazinyl, indolyl, isoindolyl, indazolyl, benzofuranyl, isobenzofuranyl, purinyl, quinazolinyl, quinolyl, isoquinolyl, benzoimidazolyl, benzothiazolyl, benzothiophenyl, thianaphthenyl, benzoxazolyl, benzisoxazolyl, cinnolinyl, phthalazinyl, naphthyridinyl, and quinoxalinyl. Included within the definition of "heteroaryl" are fused ring systems, including, for example, ring systems in which an aromatic ring is fused to a heterocycloalkyl ring. Examples of such fused ring systems include, for example, phthalamide, phthalic anhydride, indoline, isoindoline, tetrahydroisoquinoline, chroman, isochroman, chromene, and isochromene.

As used herein, the term "subject" refers to a warm blooded animal such as a mammal, preferably a human, or a human child, which is afflicted with, or has the potential to be afflicted with one or more diseases and conditions described herein.

As used herein, a "therapeutically effective amount" refers to an amount of a compound of the present invention effective to prevent or treat the symptoms of particular disorder.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

All other terms used in the description of the present invention have their meanings as is well known in the art.

In another aspect, the present invention is directed to pharmaceutically acceptable salts of the compounds described above. As used herein, "pharmaceutically acceptable salts" includes salts of compounds of the present invention derived from the combination of such compounds with non-toxic acid.

Acid addition salts include inorganic acids such as hydrochloric, hydrobromic, hydroiodic, sulfuric, nitric and phosphoric acid, as well as organic acids such as acetic, citric, propionic, tartaric, glutamic, salicylic, oxalic, methanesulfonic, para-toluenesulfonic, succinic, and benzoic acid, and related inorganic and organic acids.

In addition to pharmaceutically-acceptable salts, other salts are included in the invention. They may serve as intermediates in the purification of the compounds, in the preparation of other salts, or in the identification and characterization of the compounds or intermediates.

The pharmaceutically acceptable salts of compounds of the present invention can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent. Such solvates are within the scope of the present invention.

It is recognized that compounds of the present invention may exist in various stereoisomeric forms. As such, the compounds of the present invention include both diastereomers and enantiomers. The compounds are normally prepared as racemates and can conveniently be used as such, but individual enantiomers can be isolated or synthesized by conventional techniques if so desired. Such racemates and individual enantiomers and mixtures thereof form part of the present invention.

It is well known in the art how to prepare and isolate such optically active forms. Specific stereoisomers can be prepared by stereospecific synthesis using enantiomerically pure or enantiomerically enriched starting materials. The specific stereoisomers of either starting materials or products can be resolved and recovered by techniques known in the art, such as resolution of racemic forms, normal, reverse-phase, and chiral chromatography, recrystallization, enzymatic resolution, or fractional recrystallization of addition salts formed by reagents used for that purpose. Useful methods of resolving and recovering specific stereoisomers described in Eliel, E. L.; Wilen, S. H. *Stereochemistry of Organic Compounds*; Wiley: New York, 1994, and Jacques, J, et al. *Enantiomers, Racemates, and Resolutions*; Wiley: New York, 1981, each incorporated by reference herein in their entireties.

Synthesis

The compounds of the present invention may be prepared in a number of methods well known to those skilled in the art, including, but not limited to those described below, or through modifications of these methods by applying standard techniques known to those skilled in the art of organic synthesis. The appropriate modifications and substitutions will be readily apparent and well known or readily obtainable from the scientific literature to those skilled in the art.

In particular, such methods can be found in R. C. Larock, *Comprehensive Organic Transformations*, Wiley-VCH Publishers, 1999.

All processes disclosed in association with the present invention are contemplated to be practiced on any scale, including milligram, gram, multigram, kilogram, multikilogram or commercial industrial scale.

It will be appreciated that the compounds of the present invention may contain one or more asymmetrically substituted carbon atoms, and may be isolated in optically active or racemic forms. Thus, all chiral, diastereomeric, racemic forms, isomeric forms of a structure are intended, unless the specific stereochemistry or isomeric form is specifically indicated. It is well-known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

Compounds of the present invention may be prepared by a variety of synthetic routes. The reagents and starting materials are commercially available, or readily synthesized by well-known techniques by one of ordinary skill in the arts. All substituents, unless otherwise indicated, are as previously defined.

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in *Protective Groups in Organic Chemistry*, 3rd ed., John Wiley and Sons, 1999; J. F. W. McOmie in *Protective Groups in Organic Chemistry*, Plenum Press, 1973.

The general routes to prepare the examples of the present invention are shown in the Scheme A hereafter. The reagents and starting materials are commercially available, or readily synthesized by well-known techniques by one of ordinary skill in the arts. All substituents in the synthetic Schemes, unless otherwise indicated, are as previously defined.

EXAMPLES

Figure 1:
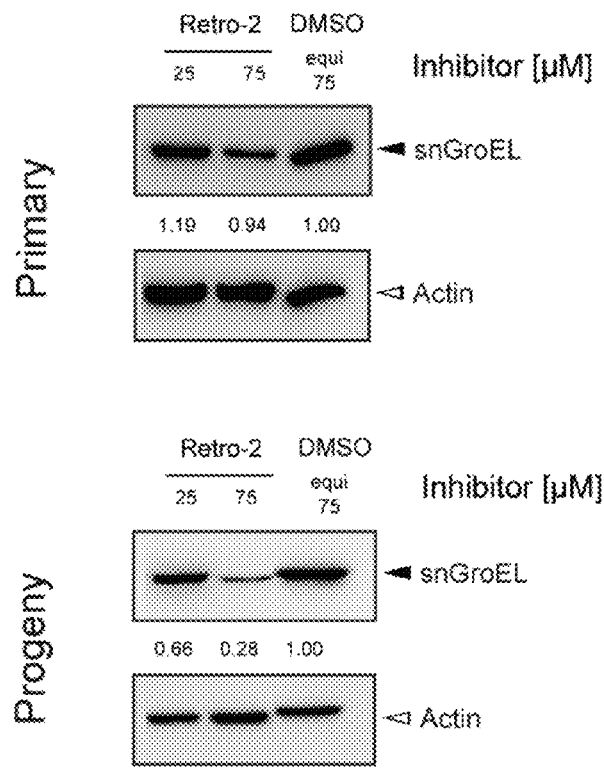
FIG. 1 shows the effect of Retro-2 on the Sn bacterial load of infected HeLa cells by bacterial GroEL immunoblot and Actin used as a loading control.

I. Synthesis of Compounds of Formula (I)

A general scheme for the synthesis of compounds described herein is as follows (more details can be found in N-methyl dihydroquinazolinones derivatives of Retro-2 with enhanced efficacy against Shiga toxin., R. Noel, N. Gupta, V. Pons, A. Goudet, M. D. Garcia-Castillo, A. Michau, J. Martinez, D. A. Buisson, L. Johannes, D. Gillet, J. Barbier, J.-C. Cintrat, *J. Med. Chem.*, 2013, 56(8), 3404-3413)

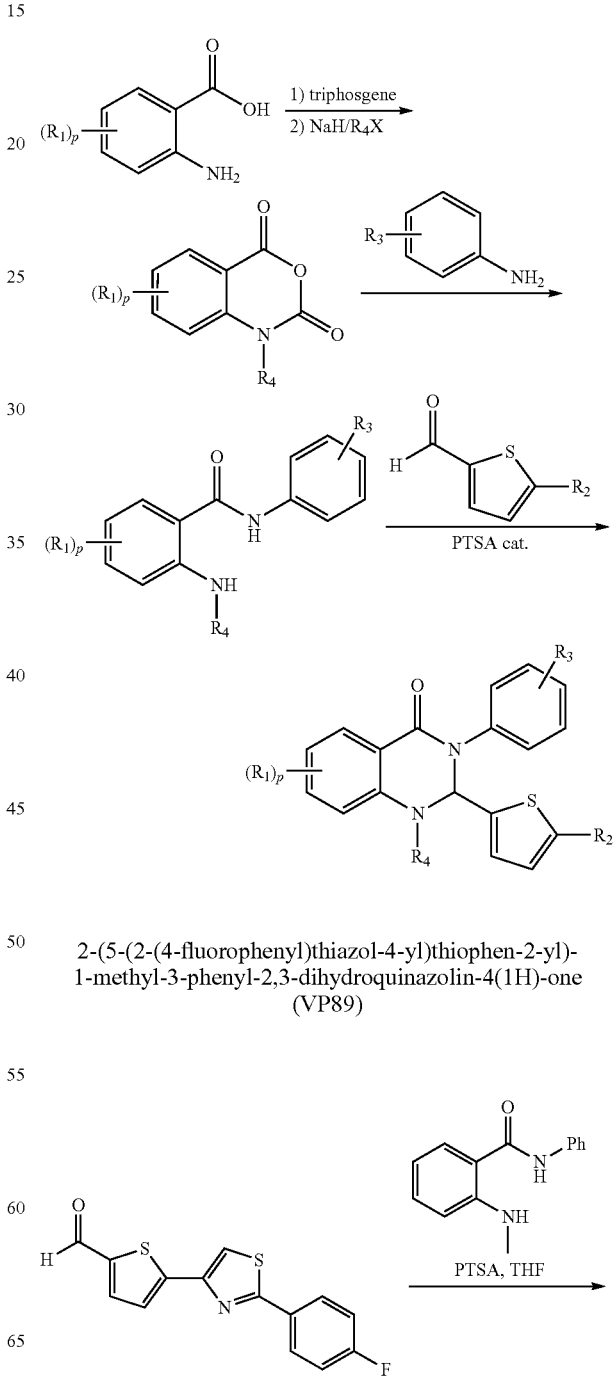

2-(5-(2-(4-fluorophenyl)thiazol-4-yl)thiophen-2-yl)-1-methyl-3-phenyl-2,3-dihydroquinazolin-4(1H)-one (VP89)

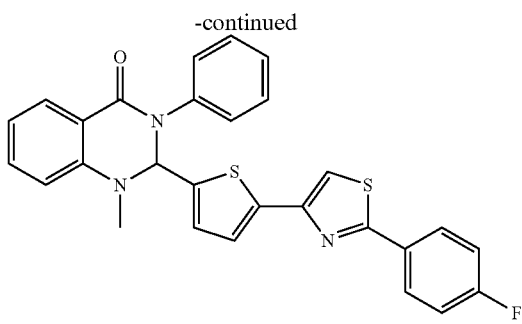

To a solution of 5-(2-(4-fluorophenyl)thiazol-4-yl)thiophene-2-carbaldehyde (227 mg, 0.787 mmol) in THF (5 mL), was added 2-(methylamino)-N-phenylbenzamide (311 mg, 1.377 mmol) and p-toluenesulfonic acid (27 mg, 0.157 mmol). The mixture was refluxed overnight, then neutralized with a saturated solution of NaHCO$_3$ (10 mL) and extracted with ethyl acetate (3×20 mL). The organic layer was concentrated under vacuum, dried over Na$_2$SO$_4$, filtrated and concentrated under vacuum. The crude mixture was purified by flash chromatography (cyclohexane-ethyl acetate, 1-0 to 7-3) affording the desired compound (165 mg, 42%).

$^1$H-NMR (400 MHz, DMSO) δ (ppm)=2.99 (s, 3H), 6.51 (s, 1H), 6.78 (d, J=8.1 Hz, 1H), 6.92 (t, J=7.3 Hz, 1H), 6.99 (d, J=3.8 Hz, 1H), 7.26-7.36 (m, 5H), 7.38-7.44 (m, 3H), 7.46 (td, J=7.8 Hz, J'=1.6 Hz, 1H), 7.90 (dd, J=7.8 Hz, J'=1.6 Hz, 1H), 7.92-7.97 (m, 3H).

$^{13}$C-NMR (100 MHz, DMSO) δ (ppm)=35.5, 76.2, 113.7, 114.4, 116.6, 116.9, 117.2, 119.1, 124.2, 126.9, 127.2, 128.6, 128.7, 128.9, 129.0, 129.3, 129.5, 129.5, 134.8, 137.8, 140.1, 140.5, 146.8, 149.6, 161.2, 162.5, 165.0, 166.5

MS (ESI) [M+H]$^+$=498.12
LC/MS (X-bridge 100×4.6 mm)
Gradient A: $t_R$=24.37 min
Gradient D: $t_R$=21.35 min
I.R. (neat, cm$^{-1}$) 1639, 1601, 1491, 1227, 1156, 742, 691.

II. Biological Activity against Chlamydiales Infections
II.1. Materials and Methods
Cell Lines and Bacteria HeLa229 (ATCC CCL-2.1) were grown in RPMI1640 medium (Glutamax, 10% FBS, w/o HEPES) (Invitrogen). Stable HeLa229 cell lines were established to constantly label the Golgi apparatus (B4GalT1 in a pCMV6-AC-mRFP cloning vector, OriGene) and the ER (KDEL in a pDsRed2-ER expression vector).

*Simkania negevensis* (Sn) strain Z (ATCC VR-1471) was prepared as described previously (Mehlitz A, Karunakaran K, Herweg J A, Krohne G, van de Linde S, Rieck E, Sauer M, Rudel T. The chlamydial organism Sn forms ER vacuole contact sites and inhibits ER-stress. Cell Microbiol 2014; 16(8):1224-1243).

Briefly, HeLa229 cells were grown to 50-70% confluence, were inoculated with Sn in RPMI1640 with 5% FBS, for 6 h at 35° C. in a humidified incubator at 5% CO$_2$. Medium was replaced by infection medium (RPMI1640, Glutamax, 5% FBS, w/o HEPES) and growth was allowed for 3 days. Cells were mechanically detached and bacteria were released using ~2-5 mm glass beads (Carl Roth). Low speed supernatant (600×g, 4° C. and 5 min) was subjected to high-speed centrifugation (20,000×g, 4° C. and 30 min) to pellet bacteria. Bacteria were washed twice with 5 ml SPG (250 mM sucrose, 50 mM sodium phosphate, 5 mM glutamate, pH 7.4), aliquoted and stored at −80° C. in SPG.

*Chlamydia trachomatis* (Ctr). Laboratory-adapted strain L2/434/Bu (ATCC VR902B) was used in assays. Full biological and genetic information is available for this strain including complete genome sequence and defined proteome. This strain has a relatively low particle to infectivity ratio, perform efficient cell infection and has a higher viability than standard genital tract isolates with faster developmental cycle. Culture conditions have been described in (Wang Y., Kahane S., Cutcliffe L. T., Skilton R. J., Lambden P. R., Clarke I. N. Development of a transformation system for *Chlamydia trachomatis*: Restoration of glycogen biosynthesis by acquisition of a plasmid shuttle vector. PLoS Pathogen, 2011, 7(9):e1002258. doi: 10.1371/journal.ppat.1002258).

Sn Infectivity Assays in Presence of Compound According to the Present Invention 40,000 HeLa cells were seeded in 12-well cluster plates, inhibitor-treated and infected as indicated in the respective experiments.

Figure 2:
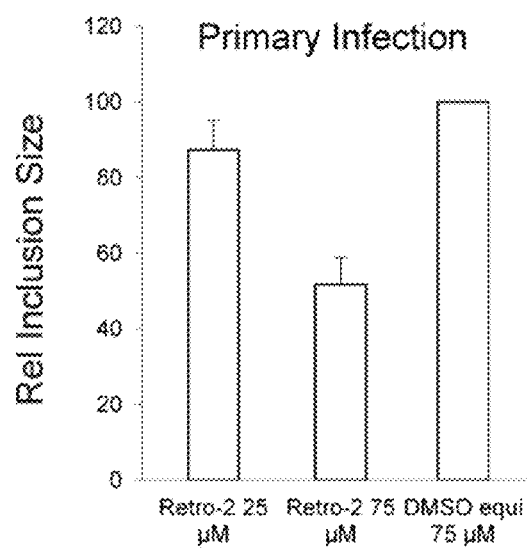
FIG. 2 shows the effect of Retro-2 on the Sn inclusion size during primary infection of HeLa cells.
Figure 3:
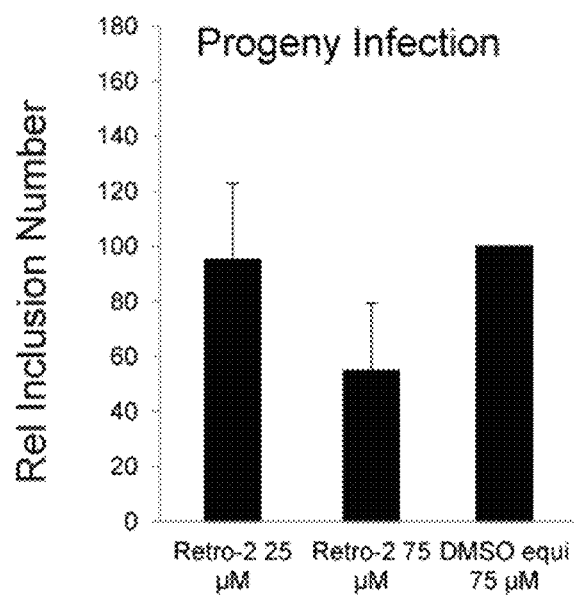
FIG. 3 shows the effect of Retro-2 on the number of Sn inclusions during progeny infection of HeLa cells
Figure 4:
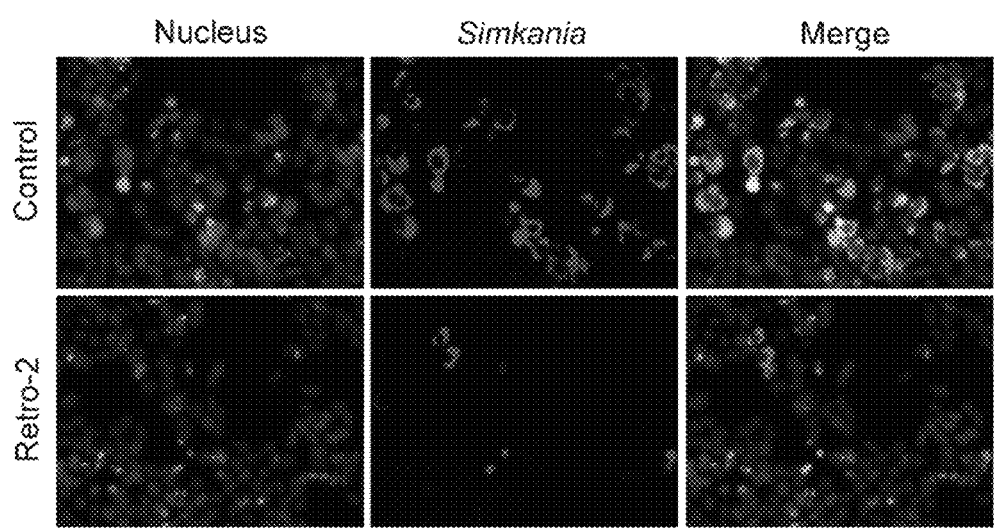
FIG. 4 shows pictures illustrating effect of Retro-2 on phenotypic variations in Sn inclusion formation in infected HeLa cells.

For infectivity assays cells were either fixed and stained at indicated time points (FIG. 2, 4; inclusion formation/primary infection) or bacteria were released via one freeze thaw cycle (−70° C./37° C.) followed by mechanical release through pipetting and transfer to fresh HeLa229 cells (1:25-1:50, progeny/infectivity). Cells were centrifuged for 1 h at 35° C. and medium exchanged to infection medium. Progeny was fixed at day 3 post infection and processed for staining (FIG. 3) or harvested for immunoblotting (FIG. 1). Infectivity assays were imaged on an automated fluorescence microscope Leica DMIR (FIG. 4). Numbers and average sizes of the SCV as well as host cell numbers were determined via GroEL and DAPI staining and images were analysed and quantified using FIJI (ImageJ) and Excel (Microsoft).

In progeny assay, bacteria are first grown in HeLa229 cells treated with inhibitors (Retro-2 at a concentration of 25 and 75 μM) and the infectious particles from this primary infection are applied to fresh cells in the absence of inhibitor to measure the bacterial load (GroEL immunoblot) and inclusion formation (immunofluorescence microscopy).

*Chlamydia trachomatis* (Ctr) Infectivity Assays in Presence of Compound According to the Present Invention Compound application during Ctr infection. HeLa229 cells were pretreated with Retro-2 in concentrations of 25, 50 and 75 μM for 30 min until Ctr (MOI1) were added to the cells. Compounds were present during infection.

Figure 6:
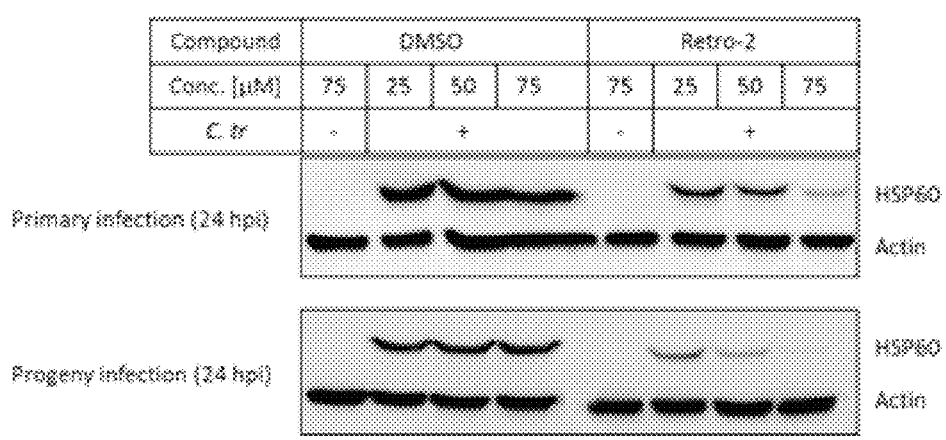
FIG. 6 shows immunotblot analysis of lysed HeLa cells after Ctr primary and progeny infection in presence of Retro-2; Chlamydial growth was detected with antibodies against chlamydial HSP60 protein and Actin was used as loading control.

(A) Cells with primary infection were lysed 24 h post infection (hpi). To obtain progeny infection compound treated cells were lysed 48 hpi and lysate was used to infect fresh HeLa229 cells. Progeny infection was lysed 24 hpi and analyzed together with primary infection samples by immunoblot. Chlamydial growth was detected with antibodies against chlamydial HSP60 protein and Actin was used as loading control (FIG. 6).

Figure 7:
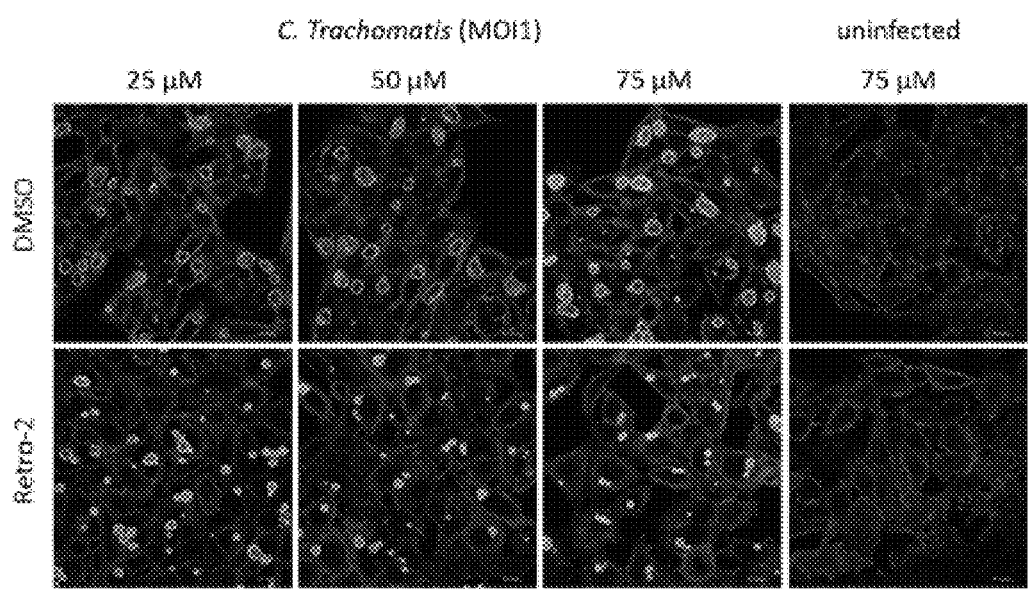
FIG. 7 shows pictures of Ctr infected HeLa cells after Alexa-680 coupled Phalloidin staining; Ctr are detected by GFP-signal.

(B) Infected cells were fixed with 4% Paraformaldehyde 24 hpi. Cells were stained by Alexa-680 coupled Phalloidin and Ctr were detected by GFP-signal (FIG. 7).

II.2. Results
Infection by Sn

Figure 5:
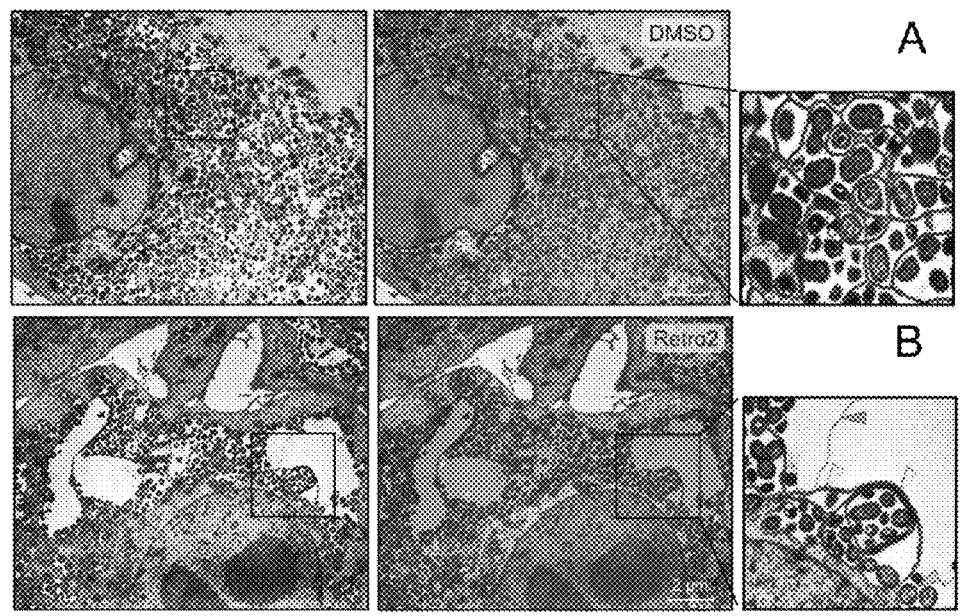
FIG. 5 shows pictures of the subcellular structure of Sn inclusions in infected HeLa cells by transmission electron microscopy in presence of DMSO or of Retro-2.

Tested inhibitor of retrograde transport Retro-2 has had an inhibitir effect on primary and progeny infection for Sn (FIGS. 1, 2, 3 and 4). This was shown by western detection of Sn GroEL (FIG. 1), relative Sn inclusion sizes in primary infection (FIG. 2), relative Sn inclusion number in progeny infection (FIG. 3), fluorescence microscopy (FIG. 4) and transmission electron microscopy (TEM; FIG. 5).

The maximal inhibition of Sn replication was observed at a concentration of 75 μM (FIGS. 1, 2, 3 and 4).

Sn inclusions formed normally in DMSO-treated control cells. Retro-2 affected the Sn inclusions morphology since sub-vacuolar membranes were highly enlarged and contained excessive membrane material, probably as a consequence of defective membrane fusion and vacuole formation (FIG. 5). Parts of the enlarged sub-vacuoles contained just few bacteria located at the inclusion boundary which may indicate defective Sn replication. Additionally, sub-vacuoles were surrounded by multiple membranes at several areas indicative of a role of Retro-2 inhibited pathways in Sn inclusions formation and membrane fusion defect.

In summary, Retro-2 compound inhibits primary and progeny infection for Sn.

Infection by *Chlamydia trachomatis*

Experiments performed to test the anti-chlamydial activity of Retro-2 demonstrated a strong inhibitory effect of Retro-2 on Ctr development (FIGS. 6 and 7). This was shown by western detection of Ctr Hsp60 in infected cells (FIG. 6) and staining of Ctr inclusions with GFP-expressing Ctr (FIG. 7).

This treatment of the primary Ctr infection also resulted in significant consequences of the progeny infection (FIG. 6); Retro-2 which blocks chlamydial replication in the primary infection consequently shows highly reduced amounts of Ctr in the progeny with almost no Ctr Hsp60 detection at 75 μM of Retro-2.

These results highlight the utility of Retro-2 as an anti-chlamydial compound. The results depicted in FIGS. 6 and 7 reveal that Retro-2 affects different cellular mechanisms and have various targets which are important at defined stages of the chlamydial developmental cycle.

III. Biological Activity against Chlamydiales Infections

III.1. Materials and Methods

Cell Lines and Bacteria

HeLa229 (ATCC CCL-2.1). Cells were grown in RPMI1640 medium (Glutamax, 10% FBS, w/o HEPES) (Invitrogen).

*Chlamydia trachomatis* (Ctr). Laboratory-adapted strain L2/434/Bu (ATCC VR902B) was used in assays. Full biological and genetic information is available for this strain including complete genome sequence and defined proteome. This strain has a relatively low particle to infectivity ratio, perform efficient cell infection and has a higher viability than standard genital tract isolates with faster developmental cycle. Culture conditions have been described in (Wang Y., Kahane S., Cutcliffe L. T., Skilton R. J., Lambden P. R., Clarke I. N. Development of a transformation system for *Chlamydia trachomatis*: Restoration of glycogen biosynthesis by acquisition of a plasmid shuttle vector. PLoS Pathogen, 2011, 7(9):e1002258. doi: 10.1371/journal.p-pat.1002258).

*Chlamydia trachomatis* (Ctr) Infectivity Assays in Presence of Compounds According to the Present Invention Compound application during *Chlamydia trachomatis* infection. HeLa229 cells were pretreated with Retro-2 and Retro-2 derivatives in concentrations of 25 μM for 1 hour until *Chlamydia trachomatis* (MOI1) were added to the cells. Compounds were present during infection. To obtain progeny infection, compound treated cells were lysed 24 h post infection (hpi) and lysate was used to infect fresh HeLa 229 cells. Infected cells of progeny infection were fixed with 4% Paraformaldehyde 48 hpi. Cells were stained for DAPI and *Chlamydia trachomatis* were detected by GFP-signal. Images are representative of n=2 independent experiments. Quantification of infected cells by *Chlamydia trachomatis* was realized from microscopy images with Image J software (FIG. 8) and cellular protection by compounds at 25 μM was then determined (Table 1) by comparison with solvent-treated cells (control) with the following equation:

$$\text{Cellular protection} = 100 - \frac{\text{\% of infected cells in presence of inhibitor}}{\text{\% of infected cells in control}} \times 100$$

III.2. Results

TABLE 1

| | Cellular protection at 25 μM (%) |
|---|---|
| Retro-2 | 18.1 |
| Retro-2.1 | 100 |
| RN-2-016 | 91.8 |
| RN-3-072 | 100 |
| Compound 25 | 100 |
| VP-89 | 88.5 |

Figure 8:
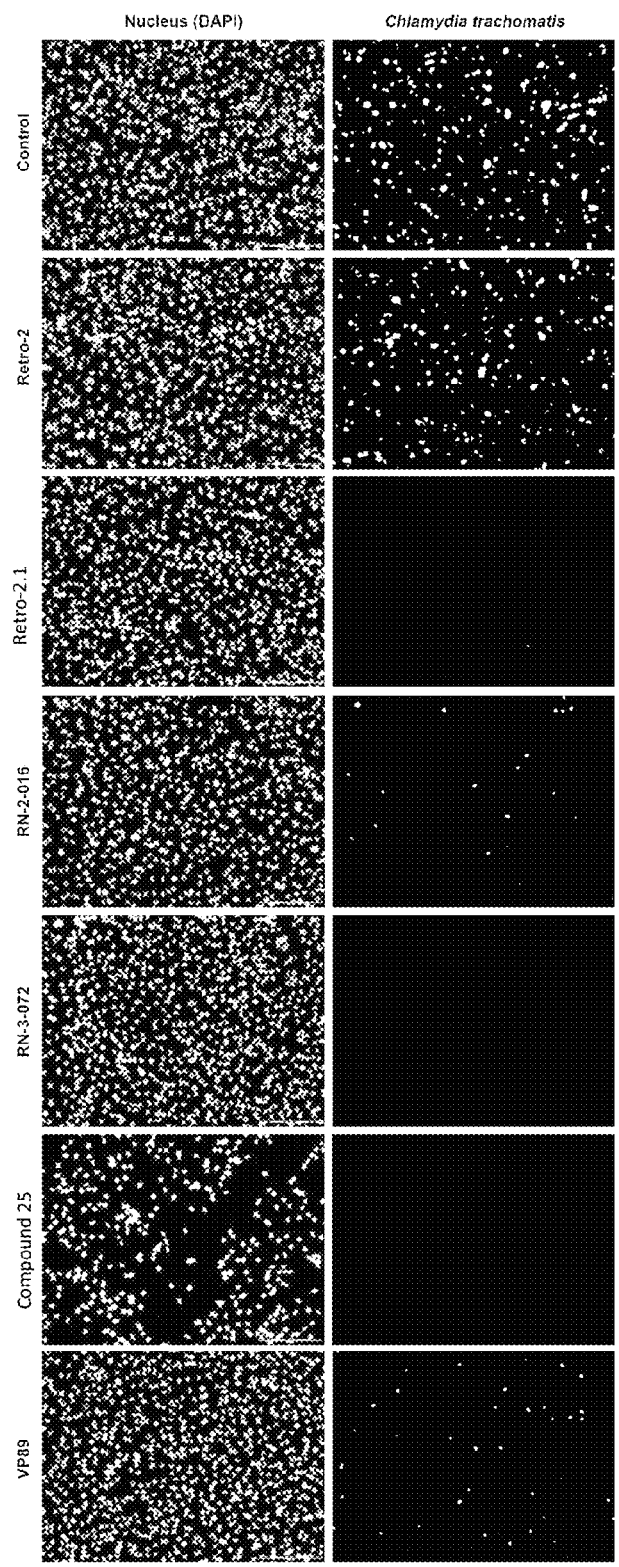
FIG. 8 shows microscopy images of cells stained for DAPI and *Chlamydia trachomatis* (detected by GFP-signal) after Retro-2 and Retro-2 derivatives derivatives application at 25 μM during *Chlamydia trachomatis* infection of HeLa229 cells.

This treatment of the primary Ctr infection with Retro-2 derivatives resulted in a strong consequences of the progeny infection at 25 μM in comparison with Retro-2 (FIG. 8).

Conclusion

These results highlight the utility of Retro-2 derivatives of formula (I') as an anti-chlamydial compound. The results depicted in FIG. 8 that Retro-2 derivatives are much more potent than Retro-2 at low concentration and affect cellular mechanisms that are important at defined stages of the chlamydial developmental cycle.

The invention claimed is:

1. A method for treating a Chlamydiae infection comprising the administration of a therapeutically effective amount of a compound of formula (I) to a subject in need thereof

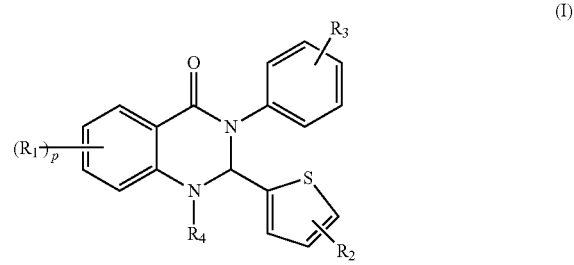

(I)

Wherein:

$R_1$ is at each occurrence, independently selected from H, Cl, Br, I, F;

$R_2$ is independently selected from Br and 5 to 10 membered heteroaryl, said 5 to 10 membered heteroaryl groups being optionally substituted by one to three $R_5$;

$R_3$ is independently selected from H, F, Cl, Br, I, $C_1$-$C_6$ alkyl;

$R_4$ is, at each occurrence, independently selected from H, $C_1$-$C_6$ alkyl;

$R_5$ is independently selected from F, Cl, Br, I, $C_1$-$C_6$ alkyl, $C_6$-$C_{10}$ aryl, said aryl group being optionally substituted by one to three $R_6$;

$R_6$ is F, Cl, Br, I;

p is 1, 2 or 3;

and the stereoisomeric forms, mixtures of stereoisomeric forms or pharmaceutically acceptable salts forms thereof, providing said compound is not of the following formula:

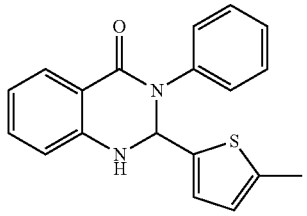

2. The method of claim 1, wherein the Chlamydiae infection is a *Chlamydia* or *Simkania* infection.

3. The method of claim 1, wherein at least one of $R_1$ is H or F.

4. The method of claim 1, wherein $R_2$ is a 5 to 10 membered heteroaryl.

5. The method of claim 4, wherein $R_2$ is 1,3-thiazolyl.

6. The method of claim 1, which is selected from the group consisting of:
- 6-fluoro-1-methyl-2-(5-(2-methylthiazol-4-yl)thiophen-2-yl)-3-phenyl-2,3-dihydroquinazolin-4(1H)-one;
- 2-(5-(2-methylthiazol-4-yl)thiophen-2-yl)-3-phenyl-2,3-dihydroquinazolin-4(1H)-one;
- 2-(5-bromothiophen-2-yl)-1-methyl-3-phenyl-2,3-dihydroquinazolin-4(1H)-one;
- 3-(2-chlorophenyl)-1-methyl-2-(5-(2-methylthiazol-4-yl)thiophen-2-yl)-2,3-dihydroquinazolin-4(1H)-one; and
- 2-(5-(2-(4-fluorophenyl)thiazol-4-yl)thiophen-2-yl)-1-methyl-3-phenyl-2,3-dihydroquinazolin-4(1H)-one.

7. A pharmaceutical composition comprising a compound of formula (Ia):

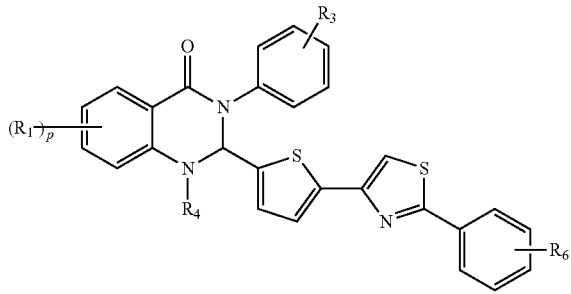

(Ia)

Wherein:

$R_1$, $R_3$, $R_4$, $R_6$, and p are as defined in formula (I) in claim 1, $R_4$ is independently selected from H or $C_1$-$C_6$ alkyl, and the stereoisomeric forms, mixtures of stereoisomeric forms or pharmaceutically acceptable salts forms thereof, in admixture with one or more pharmaceutically acceptable excipients.

8. The pharmaceutical composition of claim 7, wherein $R_4$ is $C_1$-$C_6$ alkyl, notably methyl.

9. The pharmaceutical composition of claim 7, wherein $R_3$ is H.

10. The pharmaceutical composition of claim 7, wherein $R_1$ is H.

11. The pharmaceutical composition of claim 7, wherein the compound of formula (Ia) is 2-(5-(2-(4-fluorophenyl)thiazol-4-yl)thiophen-2-yl)-1-methyl-3-phenyl-2,3-dihydroquinazolin-4(1H)-one (VP89).

12. A compound of formula (Ia):

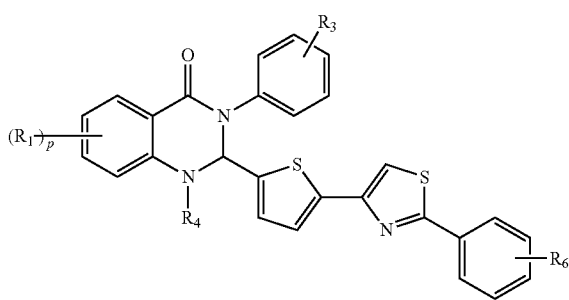

(Ia)

Wherein:

$R_1$, $R_3$, $R_4$, $R_6$, and p are as defined in formula (I) in claim 1, $R_4$ is independently selected from H or $C_1$-$C_6$ alkyl, and the stereoisomeric forms, mixtures of stereoisomeric forms or pharmaceutically acceptable salts forms thereof.

13. The method of claim 4, wherein $R_2$ is 4-(1,3-thiazolyl).

* * * * *